United States Patent [19]

Higgins

[11] 4,455,373

[45] Jun. 19, 1984

[54] MICROBIOLOGICAL OXIDATIONS

[75] Inventor: Irving J. Higgins, Wingham, England

[73] Assignee: Imperial Chemical Industries PLC, London, England

[21] Appl. No.: 288,205

[22] Filed: Jul. 29, 1981

[30] Foreign Application Priority Data

Aug. 1, 1980 [GB] United Kingdom ............... 8025241

[51] Int. Cl.³ .......................... C12P 7/00; C12N 1/36; C12N 1/20
[52] U.S. Cl. .................................. 435/132; 435/136; 435/155; 435/156; 435/157; 435/245; 435/253
[58] Field of Search ............... 435/132, 136, 155–157, 435/245, 248, 253

[56] References Cited

U.S. PATENT DOCUMENTS

| | | | |
|---|---|---|---|
| 3,816,252 | 6/1974 | Moran et al. ................. | 435/248 X |
| 3,930,947 | 1/1976 | Moringa et al. ............... | 435/248 |
| 4,042,458 | 8/1977 | Harrison et al. .............. | 435/253 X |
| 4,250,259 | 2/1981 | Hou et al. ..................... | 435/253 X |
| 4,268,630 | 5/1981 | Patel et al. .................... | 435/253 X |
| 4,347,319 | 8/1982 | Hou et al. ..................... | 435/253 X |

*Primary Examiner*—Robert A. Yoncoskie
*Attorney, Agent, or Firm*—Cushman, Darby & Cushman

[57] ABSTRACT

Microbiological oxidations of organic compounds including C6 to C28 alkanes, C2 to C18 alkenes and cyclic compounds such as cyclohexane and benzene carried out using as catalysts methane-utilizing bacteria adapted to utilize methanol as a carbon source. The application also covers methane-utilizing bacteria adapted to utilize methanol as a carbon source and a method for producing such bacteria. In the method methane-utilizing bacteria are cultured in the presence of methanol vapor as principal carbon source for sufficient time to allow adaptation to occur.

8 Claims, No Drawings

MICROBIOLOGICAL OXIDATIONS

This invention relates to microbiological oxidations carried out in the presence of methane-utilizing bacteria adapted to utilize methanol as a carbon source for growth or enzyme extracts of such microorganisms, to methane utilizing bacteria adapted to utilize methanol as a carbon source for growth and to a method for adapting methane utilizing bacteria to utilize methanol as a carbon source for growth.

Bacteria capable of utilizing methane as a source of carbon and energy have been known for many years. Such bacteria include strains of the species *Methylosinus trichosporium* and *Methylococcus capsulatus* and are generally known as "methylotrophs", the classification system for them proposed by R Whittenbury et al (J. Gen. Microbiol. 61, 205–218, (1970) being widely accepted. Whilst such bacteria cannot usually utilize more complex carbon sources, such as ethane, for growth, early workers in this art found that they were capable of oxidising a limited number of simple organic molecules, for example ethane and propane. These oxidations are discussed in a number of papers including those by R Whittenbury et al (cited above) and by A W Thomson et al (Arch. Microbiol., 109, 243–246, (1976)). More recently it has been found that, surprisingly methane-utilizing bacteria and enzyme extracts thereof are capable of oxidizing more complex organic compounds than had previously been considered possible. This has increased interest in these microorganisms and considerable research effort has been devoted to the study of their use in oxidations in recent years. The oxidation of a wide range of organic compounds using methane-utilizing strains of *Methylosinus trichosporium* and enzyme extracts thereof is described and claimed in our co-pending U.K. patent application published as Serial No. 2024205A.

Oxidations in the presence of methane-utilizing bacteria, for instance the process of Serial No. 2024205A, can be used to produce many useful products. We believe that these oxidations are catalysed by the enzyme methane mono-oxygenase (MMO) contained in the cells of methane-utilizing bacteria or in enzyme extracts thereof. Whilst it has been found to be possible to grow these bacteria using methanol as a carbon source, it has been generally believed that bacteria grown in this way do not express MMO and hence are ineffective in oxidations. There are few comments in the literature about the presence or absence of MMO in methanol-grown obligate methylotrophs. It is stated to be absent in a number of publications e.g. Hou et al, Appl. Environ. Microbiol., 38, 127, 1979 and Patel et al, Appl. Environ. Microbiol., 39, 720, 1980. However there has been a report of its presence in one strain *Methylococcus capsulatus* NCIB 11083 (Linton and Vokes, FEMS Microbiol. Lett., 4, 125, 1978). To date however it has been considered to be necessary to grow the bacteria for use in oxidations in the presence of methane. This has a number of disadvantages since it entails fermentation with a gaseous nutrient and involves an explosion risk.

We have now found that it is possible to adapt methane-utilizing bacteria to enable them to utilize methanol as a sole carbon source for growth without suppressing their ability to express the enzyme MMO.

According to the present invention we provide a process for the oxidation of an oxidsable organic compound containing at least two carbon atoms by contacting the compound under aerobic conditions with cells of a methane-utilizing bacterium containing oxygenase enzyme activity or with an enzyme extract thereof wherein the bacterium has been adapted to utilize methanol as a carbon source for growth by cultivating it in a culture medium in the presence of methanol vapour as the principal and preferably the only carbon source for a period sufficient to allow adaptation to occur.

Also according to the invention we provide methane-utilizing bacteria containing oxygenase enzyme activity which have been adapted to utilize methanol as a carbon source for growth by cultivation in a culture medium in the presence of methanol vapour as the principal and preferably the only carbon source for a period sufficient to allow adaptation to occur.

Also according to the invention we provide a method for the adaptation of methane-utilizing bacteria containing oxygenase enzyme activity to utilize methanol as a carbon source for growth wherein the bacteria are cultured in a culture medium in the presence of methanol vapour as the principal and preferably the only carbon source for a period sufficient to allow adaptation to occur.

Suitably the method of the invention is operated by inoculating a culture medium, containing all essential nutrients with the exception of carbon, with cells of a methane-utilizing bacterium and agitating the inoculated medium in the presence of methanol vapour. On a laboratory scale this can be done in a flask having a centre well. The inoculated medium is placed in the main body of the flask and methanol is placed in the centre well, thus enabling methanol vapour escaping from the centre well to contact the inoculated medium. The medium can be agitated by mechanical shaking. If necessary the methanol in the centre well may be diluted with water to reduce the risk of damage to cells in the medium in the event of methanol spillage caused by shaking. Some cells in the medium adapt to methanol as a carbon source, grow and multiply in number over a number of generations to produce eventually a culture of cells adapted to utilize methanol as its carbon source for growth which can be supplied with methanol in the liquid phase. Preferably after adaptation methanol is supplied to the culture in gradually increasing concentrations during an initial period. The adapted cells can then be used in the oxidation process, if necessary being separated from the medium and supplied continuously to the oxidation process which can be carried out continuously in a reactor located close to that in which the adapted cells are grown.

Methane-utilizing bacteria which may be adapted by the method of the invention include strains of the species *Methylosinus trichosporium* and *Methyloccoccus capsulatus*, particularly *Methylosinus trichosporium* strain OB 3b and *Methylococcus capsulatus* (Bath strain). Cultures of OB 3b have been deposited at the National Collection of Industrial Bacteria (NCIB), Torrey Research Station, Aberdeen, Scotland, UK as NCIB 11131 and at the Fermentation Research Institute, Japan as No. 4981 (Acceptance No. 4981). A culture of the Bath strain has been deposited at NCIB as NCIB 11132. The Bath strain is referred to by J Colby and H Dalton (J. Biochem. 157, 495–497, 1976).

The period required for adaptation, i.e. until it is possible to supply methanol in the liquid phase to a culture, varies depending upon the microorganism and upon the time between successive generations of that microorganism. Generally a culture will have become adapted after 15 to 30 generations. Preferably the period allowed for adaptation is at least 7 days, especially 7 to 10 days.

The composition of the culture medium and the conditions, for example pH and temperature, during adaptation and subsequent growth vary depending upon individual bacteria. Suitable compositions and conditions can readily be determined by a competent microbiologist. For instance the preferred temperature during adaptation and subsequent growth is 30° C. for *Methylosinus trichosporium* strain OB 3b and 45° C. for *Methylococcus capsulatus* (Bath strain).

The general conditions for the oxidation process of the invention are as described in our co-pending published U.K. patent application No. 2024205A. Preferably the pH of the reaction is in the range pH 7 to 8, particularly pH 7.2, a phosphate buffer being used for preference. The relative amounts of organic compound and the cell containing medium depend upon the miscibility of the organic compound with aqueous media and its toxicity to the bacterial cells. If the compound is immiscible in water it is shaken in the aqueous medium until a suspension of fine droplets of the compound is formed therein.

The oxidation process of the invention can be used to oxidise a wide range of organic compounds. It is however most useful for the oxidation of alkanes having from 6 to 28 carbon atoms and alkenes having from 2 to 18 carbon atoms, the products being the corresponding alkanols and the corresponding epoxides respectively. Alkanes which may be oxidised include both branched and straight-chain alkanes. Substituted alkanes may also be oxidised by the process of the invention. The invention is most usefully applied to the oxidation of n-alkanes and n-alkenes, particularly n-alkanes having from 6 to 16 carbon atoms and n-alkanes 2 to 14. The product of the oxidation of an n-alkane which is preferred is the corresponding alkan-1-ol. In cases where the oxidation proceeds further to produce e.g. alkanoic acids, biomass or $CO_2$, the further oxidation may be prevented or reduced by inclusion of appropriate inhibitors in the reaction mixture. Examples of specific alkanes which may be oxidised include hexane, heptane, octane, nonane, decane, dodecane, tridecane, tetradecane and hexadecane. Alkenes which may be oxidised include straight and branched chain alkenes having terminal or internal double bonds and substituted alkenes. Preferably the oxidation is of straight chain alkanes, particularly those having from 2 to 18 carbon atoms. Oxidation occurs at the double bond.

The process of the invention is also applicable to the oxidation of cyclic organic compounds. Cyclic compounds which may be oxidised include alicyclic hydrocarbons such as cycloalkanes, and in particular cyclohexane, aromatic compounds such as benzene and substituted benzenes, for example having alkyl- or alkenyl-substituents containing up to 12 carbon atoms and/or having substituted hydroxyl groups, heterocyclic compounds such as pyridine, and compounds containing a plurality of aromatic rings, in particular naphthalene and derivatives thereof such as methyl-substituted naphthalenes. The more important classes of products obtained by the oxidation of various classes of cyclic organic compounds are: cycloalkanols, hydroxylated derivatives of aromatic compounds, heterocyclic and naphthalenic compounds.

Examples of a number of the oxidation reactions which may be carried out using the oxidation process of the invention are given in the following Table.

TABLE

| Substrate | Oxidation Product(s) |
| --- | --- |
| Benzene | Phenol |
| Benzyl alcohol | Benzaldehyde + p-hydroxybenzyl alcohol |
| o-Cresol | 5-methyl, 1.3 benzene diol |
| Hexane | Hexan-1-ol |
| Hexadecane | Hexadecane-1-ol |
| Cyclohexane | Cyclohexanol + 3-hydroxycyclohexanone |
| Cyclohexanol | 3-hydroxycyclohexanone |
| Ethylbenzene | Benzoic acid + 2-phenylethanol + Phenylacetic acid + p-hydroxyethylbenzene |
| Propylene | Propylene oxide |
| Octane | Octan-1-ol |
| Phenol | Catechol + 1,4-dihydroxy benzene |
| Pyridene | Pyridene-N—oxide |
| Toluene | Benzoic acid + p-hydroxytoluene |
| Styrene | Styrene epoxide |
| Naphthalene | 1-Naphthol |
| iso Propyl benzene | p-hydroxy isopropyl benzene |
| p-xylene | 4-methylbenzoic acid |

The invention is illustrated by the following Example.

EXAMPLE

Adaptation of cells of *Methylosinus trichosporium* Strain OB 3b (NCIB 11131) grown on methane to growth on methanol.

The basic nutrient medium employed comprises a salts solution, a trace elements solution (0.5 ml added per liter of salts solution) and aseptically added phosphate buffer. The salts and trace elements solutions were made up as follows:

| Salts solution | |
| --- | --- |
| $CaCl_2.2H_2O$ | 0.2 g/l |
| $KNO_3$ | 1.0 g/l |
| $MgSO_4.7H_2O$ | 1.0 g/l |
| Ethylene diamine tetra-acetic acid (ferrous salt) | 0.004 g/l |

| Trace elements solution | |
| --- | --- |
| Ethylene diamine tetra-acetic acid | 0.5 g/l |
| $FeSO_4.7H_2O$ | 0.2 g/l |
| $ZnSO_4.7H_2O$ | 0.01 g/l |
| $MgCl_2.4H_2O$ | 0.003 g/l |
| $H_3BO_3$ | 0.03 g/l |
| $CoCl_2.6H_2O$ | 0.02 g/l |
| $CuCl_2.2H_2O$ | 0.005 g/l |
| $NiCl_2.6H_2O$ | 0.002 g/l |
| $NaMoO_4.2H_2O$ | 0.003 g/l |

The basic nutrient medium was inoculated with a loopful of cells from a 10 day old plate grown on the basic medium and methane. 50 ml and 100 ml amounts of the thus inoculated medium were placed in a series of 250 ml centre well flasks each having 5 ml filter-sterilised methanol in its centre well. The flasks were stoppered with foil wrapped rubber bungs, placed on a shaker and incubated with shaking at 30° C. Growth occurred after between 4 and 5 days and after 7 days a thick cell suspension had been formed. At this stage cells were transferred from the centre well flasks to flasks with cotton wool bungs and grown in the basic nutrient medium containing 0.1% methanol. The concentration of methanol in the medium in the flasks was serially increased to 0.5%, 1%, 2% and finally 4%, filter sterilised methanol being added aseptically to the flasks.

The cells from the flasks were harvested, washed twice with 20 mM sodium phosphate buffer (at pH 7.0) and, after resuspending in the same buffer, were stored at 0° C. until use.

In use in the oxidation process, a washed suspension of the adapted cells containing 70-80 mg dry weight of cells in 20 ml of 20 mM sodium phosphate buffer (pH 7.0) was shaken in a 250 ml conical flask for 12 hours at 30° C. The flask was sealed when containing an atmosphere of 50% v/v air and the substrate to be oxidised when gaseous. With liquid substrates, 3 ml volumes were contained in a centre well from which they could diffuse to contact the bacterium. The products obtained were identified by combined gas chromatography and mass spectrometry. Conversion efficiencies based upon the amount of substrate entering the process, e.g. from the centre well, ranged between 70% and 90%. In this manner the following oxidations were carried out:
1. propylene to propylene oxide;
2. ethyl benzene to benzoic acid + 2-phenylethanol + phenylacetic acid + p-hydroxyethylbenzene;
3. hexadecane to hexadecone-1-ol;
4. isopropylbenzene to p-hydroxy isopropylbenzene.

I claim:

1. A process in which a hydrocarbon selected from the group consisting of alkanes, having 6 to 28 carbon atoms, alkenes having 2 to 18 carbon atoms, alicyclic hydrocarbons, benzene and alkyl benzenes is oxidized, comprising contacting the compound under aerobic conditions with cells of a methane-utilizing bacterium containing methane mono-oxygenase enzyme activity or with an extract thereof which comprises methane mono oxygenase enzyme activity wherein the bacterium has been adapted to utilize methanol as a carbon source for growth by cultivating said bacterium in a culture medium in the presence of methanol vapour as the principal carbon source for a period sufficient to allow adaptation to occur.

2. A process according to claim 1 wherein the methane-utilizing bacterium is a strain of a species selected from the group consisting of *Methylosinus trichosporium* and *Methylococcus capsulatus*.

3. A process according to claim 1 wherein the oxidisable organic compound is contacted with the adapted methane-utilizing bacterium at a pH in the range pH 7 to 8.

4. A method of adapting methane-utilizing bacteria containing oxygenase enzyme activity to utilize methanol as a carbon source for growth which comprises culturing the bacteria in a culture medium in the presence of methanol vapour as the principle carbon source for a period sufficient to allow adaptation to occur.

5. A method according to claim 4 wherein during the adaptation period methanol is the only carbon source.

6. A method according to claim 4 wherein the methane-utilizing bacteria belong to a strain of a species selected from the group consisting of *Methylosinus trichosporium* and *Methylococcus capsulatus*.

7. A method according to claim 6 wherein the methane-utilizing bacteria belong to the strain *Methylosinus trichosporium* NCIB 11131.

8. A method according to claim 4 wherein the adaptation period is a period sufficient for the growth of from 15 to 30 successive generations of the bacteria.

* * * * *